United States Patent [19]

Bucalo

[11] 4,122,850
[45] Oct. 31, 1978

[54] APPARATUS FOR PROVIDING LIVING BEINGS WITH ABSORBABLE IMPLANTS

[76] Inventor: Louis Bucalo, 155 Roberts St., Holbrook, N.Y. 11741

[21] Appl. No.: 785,290

[22] Filed: Apr. 6, 1977

Related U.S. Application Data

[60] Division of Ser. No. 693,134, Jun. 7, 1976, Pat. No. 4,030,499, which is a continuation-in-part of Ser. No. 537,572, Dec. 30, 1974, Pat. No. 3,982,537.

[51] Int. Cl.² ............................................. A61M 5/00
[52] U.S. Cl. .................................... 128/216; 128/255; 128/214 A
[58] Field of Search ................... 128/215, 214 A, 216, 128/218 R, 234, 303.12, 254, 255,

[56] References Cited

U.S. PATENT DOCUMENTS

| | | | |
|---|---|---|---|
| 1,677,642 | 7/1928 | Kirk | 128/255 |
| 1,786,373 | 12/1930 | Walker | 128/255 X |
| 2,063,902 | 12/1936 | Beasley | 128/214 A X |
| 2,078,686 | 4/1937 | Rowe | 128/255 |
| 2,078,786 | 4/1937 | Wood | 128/303.12 |

FOREIGN PATENT DOCUMENTS 813,434 9/1951 Fed. Rep. of Germany.

*Primary Examiner*—John D. Yasko
*Attorney, Agent, or Firm*—Steinberg & Blake

[57] ABSTRACT

Apparatus for providing a living being with an implant which is absorbed into the body. The implant is situated in the body adjacent the outer skin. The implant is injected in a liquid, molten condition, but assumes a solid condition at body temperature. The composition of the implant is such that the implant will be absorbed by the body at a greater rate when the temperature of the implant is increased. By situating the implant adjacent the outer skin it is possible to elevate the temperature at the outer skin so as to increase the rapidity with which the implant is absorbed by the body. A syringe which contains the implant in solid condition is provided with a heating structure which is operated for the purpose of converting the composition into a liquid molten condition in preparation for injecting the composition into body tissue.

24 Claims, 10 Drawing Figures

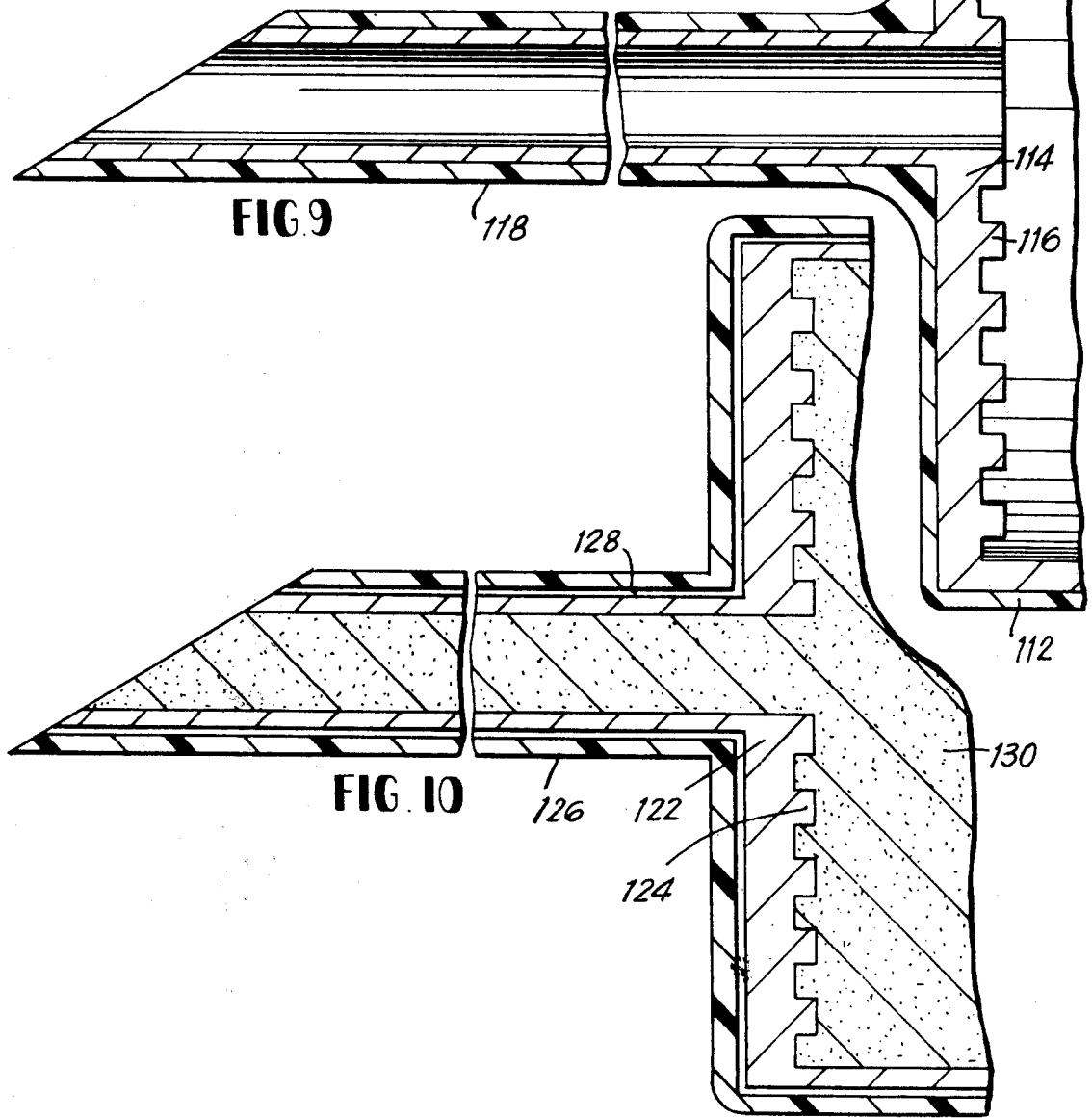

APPARATUS FOR PROVIDING LIVING BEINGS WITH ABSORBABLE IMPLANTS

CROSS REFERENCE TO RELATED APPLICATION

This application is a division of copending application Ser. No. 693,134, filed June 7, 1976, now U.S. Pat. No. 4,030,449 which is a continuation-in-part of application Ser. No. 537,572, filed Dec. 30, 1974, now U.S. Pat. No. 3,982,537.

BACKGROUND OF THE INVENTION

The present invention relates to implants of the type which are adapted to be situated in the body of a living being.

In particular, the present invention relates to implants, the composition of which is such that the implants can be absorbed by the body.

Thus, for health purposes the implant may take the form of a drug, medicament (including anesthetics), or nutrient in a carrier which at an elevated temperature will assume a molten, flowable condition facilitating injection of the composition, with the carrier assuming a solid condition at body temperature so that after injection the composition solidifies to be gradually absorbed by the body while releasing the nutrient or drug which is in particulate form and dispersed in the carrier.

However, it is also possible to provide implants for cosmetic purposes, solely in order to change the appearance of an individual in a favorable manner. Such an implant also is capable of being absorbed by the body so that the change in appearance is only temporary.

One of the problems encountered with implants of the above type is in connection with the rate at which the implant is absorbed by the body. Although implants of the above general type can be situated in the body in accordance with teachings of the above copending application, there are certain situations where it is desired to regulate the rate of absorption of the implant, and at the present time such control of the rate of absorption cannot be provided. For example in the case of a drug, mecicament, or nutrient, a physician may wish the drug, medicant, or nutrient to be absorbed by the body initially at a relatively rapid rate and thereafter at a slower rate. In the case of a cosmetic implant, after the implant has been introduced into the body tissue, the particular individual who has the implant may be unhappy with the appearance provided by way of the implant, and therefore, it may be highly desirable to be able to absorb the implant rapidly into the body so as to eliminate the change in appearance provided thereby.

A further problem encountered with implants of the general type is in connection with the structure utilized for injecting the implant into the body. At the present time, for example, it is necessary to elevate the temperature of the implant material so that it will assume a molten condition, and then this material must be handled very rapidly during injection in order to be sure that the implant material does not solidify prior to reaching the desired location in the body tissue. Furthermore, it is difficult to provide a predetermined temperature for the implant during the time when it is injected.

SUMMARY OF THE INVENTION

It is accordingly a primary object of the present invention to provide apparatus for avoiding the above drawbacks.

In particular, it is an object of the present invention to situate an absorbable implant in body tissue in such a way that the temperature of the implant can be very conveniently regulated in order to control the rapidity with which the implant is absorbed by the body.

Also it is an object of the present invention to provide an apparatus which makes it possible very conveniently to introduce the implant at a preselected temperature into the body while maintaining this temperature at a value at which the implant is in proper molten condition while it is injected.

According to the invention, the composition which forms the implant is injected into the body adjacent the outer skin, so that it assumes a solidified condition adjacent the outer skin. Then it is an extremely simple matter to elevate the temperature at the outer skin, as, for example, by applying a heating pad thereto, so that because of the proximity of the implant to the outer skin, the implant will respond to the increase in temperature of the outer skin in order to assume also an elevated temperature which will greatly reduce the time required for absorption of the implant by the body.

In addition, with the apparatus of the invention a syringe means contains the implant composition in solidified form and has connected thereto a heating means which can be operated for providing the molten condition for the implant composition so that it can be conveniently injected by the syringe means into the body tissue.

BRIEF DESCRIPTION OF DRAWINGS

The invention is illustrated by way of example in the accompanying drawings which form part of this application and in which:

FIG. 8 shows a detail of a barrel structure of a syringe which is highly effective for maintaining a desired temperature in a composition;

FIG. 9 shows yet another embodiment of the structure at the region of the needle and barrel and capable of having a good thermal insulation while also providing desired heat at the composition which is to be injected; and FIG. 10 illustrates a still further embodiment of the structure of the invention for achieving good thermal insulation while at the same time providing a good heat transmission to the composition which is injected.

DESCRIPTION OF PREFERRED EMBODIMENTS

Figure 1:
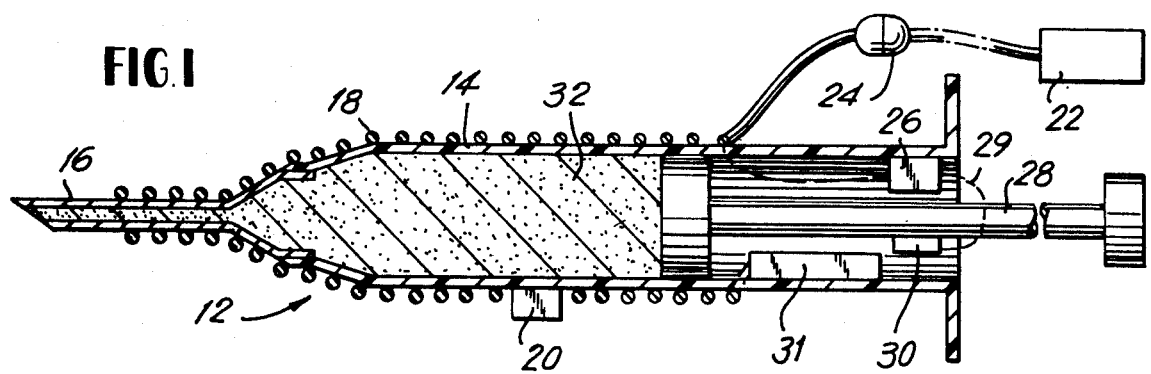
FIG. 1 is a schematic sectional illustration of one possible embodiment of a structure according to the present invention.

As has already been indicated in the above patent, there are a number of different compositions capable of being injected into the body to assume a solid condition therein while the injection takes place with the composition in a molten form. The term "molten" as used herein signifies that the composition which is solid at body temperature can assume at a temperature somewhat above body temperature an injectable, flowable condition in which the composition can be in liquid or in a semiliquid, highly viscous form. These compositions include materials such as waxes, hydrogenated oil, or the like, which are capable of being absorbed without harm by the body, and which also assume a solid condition in the body while capable of being elevated to a temperature at which these materials are in a molten form to facilitate their injection into the body. Such materials may be used by themselves for cosmetic purposes in order to change the configuration of a part of the body so as to change the appearance thereof in a desirable manner, or such materials may be used as carries for an agent, in particulate form, for example, for affecting the health of the individual, such an agent being a suitable drug, medicament, anesthetic or nutrient, for example. Thus, the agent is dissolved in or distributed in particulate form throughout the carrier material which can be elevated to assume a liquid or semiliquid form and then injected to become implanted and solidify in the body.

As has been indicated above, it is highly desirable under some conditions to increase the rapidity with which the implant is absorbed by the body. For example, in the case of a cosmetic implant, if the individual is unhappy with the implant, it is desirable to be able to disperse the implant into the body very rapidly. In the case of an implant in the form, for example, of an anesthetic, medication drug or nutrient, the physician may desire the initial dosage to be relatively high and then to be followed by a reduced dosage. This would require initial absorption at an elevated rate by the body and then subsequent absorption at a reduced rate.

In order to achieve results of the above type in accordance with the invention, the implant is injected in molten condition into the body at a location which is close to the exterior skin. Thus the implant will assume a solidified form in body tissue which is close enough to the outer skin to be influenced by an elevation of temperature at the outer skin. Thereafter, when the implant has assumed the solidified condition, if it is desired to increase the rate of absorption of the implant, it is only necessary to elevate the temperature of the skin. This can conveniently be done in any suitable way such as, for example, by applying a heating pad to the skin adjacent the location of the implant. Thus, when the temperature of the outer skin rises as a result of application of a heating pad or the like to the outer skin, the increase of temperature is transmitted through the body tissue to the implant to hasten the rate at which the latter is absorbed by the body. Thus it becomes possible in this way to increase, for example, during an initial interval of a few days subsequent to implanting, the rate at which the implant is absorbed. The added heat provided at the outer skin is transmitted to the implant to cause the latter to assume its molten form at which it is absorbed much more rapidly then when in solid form. In this way a medication or nutrient can be more rapidly absorbed by the body whenever heat is applied to the outer skin. Also if a cosmetic implant is undesired, as when in individual is unhappy with the change in the appearance resulting from the implant, it is a simple matter to apply heat to the body in order to increase the rate with which the implant will be absorbed by the body and thus will disappear.

A further advantage of the invention resides in the fact that the increase in heat of the tissue at the region of the implant will increase the blood circulation at the region of the implant, so that in the case of an implant which contains an agent which affects the health of the individual, such as a medication or nutrient, the latter agent is dispersed into blood which flows at an increased rate due to the increase in body temperature, and thus the distribution of the agent throughout the body is enhanced by these procedures.

One possible embodiment of the invention for facilitating introduction of the implant into tissue of the body is illustrated in FIG. 1. Thus, referring to FIG. 1, there is shown therein a syringe means 12 which includes a barrel 14 to which a needle 16 is connected in a well known manner. In accordance with the invention both the barrel member 14 and the needle member 16 are surrounded by an electrical heating coil 18 which can take the form of a suitable wire, although it also can take the form of a suitably electrically conductive film which becomes heated when conducting electricity. Of course the electrically conductive heating means 18 can be suitably insulated. If desired, a thermostat means 20 can be electrically connected with the electrical coil 18 so as to control the temperature thereof. The electrical coil 18 can be connected to a power source 22 such as a suitable battery, wall outlet or the like, with a control switch 24 being provided as illustrated. As is shown in phantom lines in FIG. 1, the battery 26 which can also form the power source may be situated within the barrel adjacent the outer end thereof in a manner which will not interfere with the operation of the plunger 28. In addition, the plunger 28 may carry in an electrically insulated manner a switch-operating element 30 connected by wire 29 to battery 26 and capable, in response to movement of the plunger or turning thereof, of engaging another switch element 31 for closing the circuit through the coil.

Before the plunger 28 is introduced into the barrel 14, the composition 32 which is to be injected is initially situated in the barrel. Thus the open end of the needle 16 may be closed in any suitable way and a suitable amount of composition 32 may be poured into the barrel after the composition 32 has been elevated to a temperature sufficient to assume a molten condition. Then the composition 32 can solidify within the barrel as illustrated in FIG. 1, and the plunger 28 assembled with the barrel so that the parts will have the condition shown in FIG. 1.

The assembly shown in FIG. 1, may be sold in the condition illustrated.

With the parts in the condition shown in FIG. 1, it is only necessary to energize the coil 18 so as to elevate the temperature thereof, so as to render the composition 32 molten, and then the plunger 28 can be operated to inject the molten composition into the body. Thus through this exceedingly convenient construction it is possible in a very effective manner to introduce the composition in molten condition into the body, and of course it is possible to control the temperature by way of the thermostat means 20 if desired.

Figure 2:
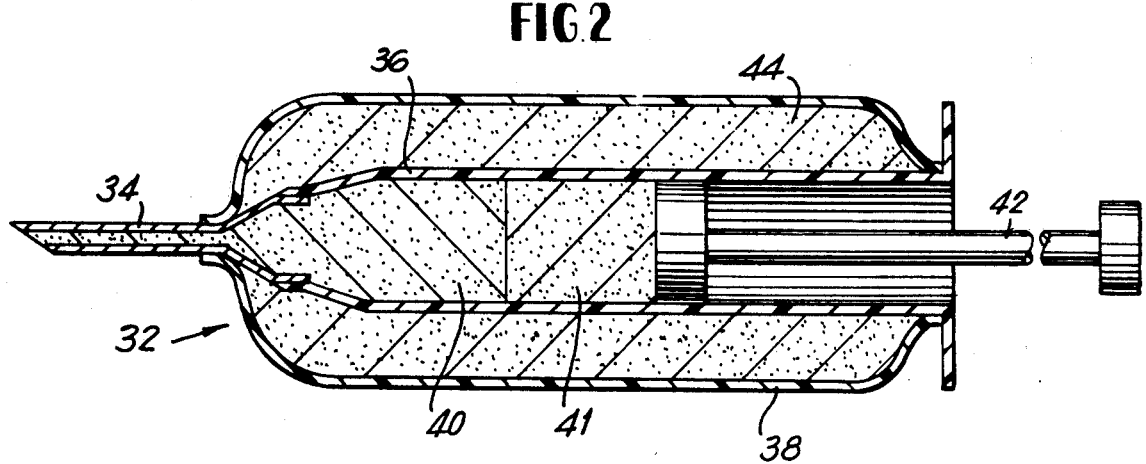
FIG. 2 is a longitudinal sectional illustration of another embodiment of the structure of the invention.

In the embodiment of the invention which is illustrated in FIG. 2 there is a syringe means 32 having a suitable injecting needle 34 operatively connected with a barrel 36 made of any suitable material. An outer fluid-tight jacket 38 surrounds the barrel member 36 and that part of the needle 34 which is connected with the barrel member. FIG. 2 also shows the composition 40 which is situated in a solid condition within the barrel 36 in advance of a second composition 41 which with composition 40 can be acted upon by the plunger 42 when the compositions 40 and 41 are rendered molten upon increasing the temperature thereof. Thus it is possible to introduce into the body tissue in one operation a plurality of drugs, medicaments, nutrients, or the like. The jacket 38 defines with the barrel 36 and the illustrated part of the needle 34 connected to the barrel 36 a hollow interior space 44 fluid-tightly closed off from the outer atmosphere and containing a thermal mass which changes its phase at the temperature at which the compositions 40 and 41 assume their molten condition. Thus, the nature of the mass 44 is such that it will change from solid to liquid form while remaining at a constant temperature which is the desired temperature at which the compositions 40 and 41 are maintained in molten form. For example, the mass 44 may be made up of various waxes or alloys of metal which are known to change phase in the above manner at a temperature which is above the temperature of the human body and sufficient to render the compositions 40 and 41 molten while still being at a temperature low enough to be received without experiencing any pain by a human being. Thus, with the above structure of FIG. 2, any suitable source of heat is provided at the jacket 38 at the exterior thereof, such as a suitable heating pad, or the like, with the source of heat being sufficient to raise the temperature of the mass 44 to the temperature at which a change in state occurs. As is well known, during the change of state such a mass will reliably remain very accurately at the predetermined temperature, and thus it is possible in this way to regulate very precisely the temperature of the compositions 40 and 41 at which they are maintained in a molten condition for injection into the body.

Figure 3:
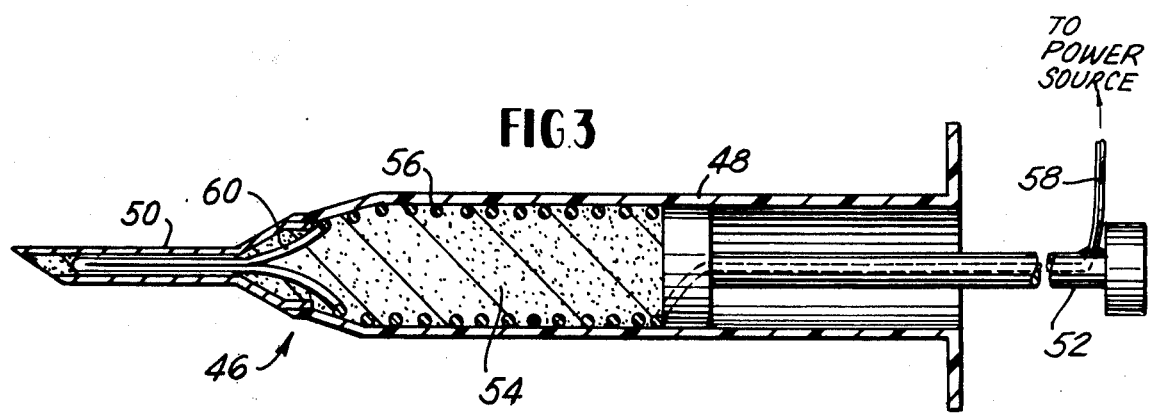
FIG. 3 illustrates in a sectional elevation a third embodiment of a structure according to the present invention.

While in the above-described embodiments of the invention, the heating means is shown at the exterior of the syringe means, in the embodiment of FIG. 3, the heating means is situated in the interior thereof. Thus, FIG. 3 shows a syringe means 46 having a barrel 48 and needle 50 which may be the same as the barrel and needle of the above-described embodiments. A plunger 52 is situated in the barrel 48, and in advance of the plunger there is situated the injectable composition 54 which after being introduced in the manner described above in liquid form will solidify to remain solid at room temperature.

However, with the construction if FIG. 3, there is also situated within the barrel 48, prior to pouring of the composition 54 into the barrel an electrical heating coil 56. Part of this coil may be extended through a suitable bore formed in the plunger 52, as illustrated in FIG. 3, when the plunger 52 is introduced into the barrel 48, so that a wire portion 58 of the coil 56 will extend outwardly beyond the plunger to be connected to a suitable power source. Thus, by energizing the heating coil 56 it is possible to transfer directly the heat to the composition 54 so as to place the latter in its molten condition. In this case, the barrel 40 is preferably made of an electrical as well as thermal insulating material, and if desired the needle 50 may also be made of an electrically insulating as well as thermally insulating material.

The nature of the coil 56 is such that it is readily compressed in response to advancing of the plunger toward the needle, so that there wil be no substantial resistance to discharge of the molten composition 54 into the body after the composition is heated upon energizing of the coil 56.

As a further feature of the invention shown in FIG. 3, part of the coil will have a wire loop portion 60 extending into the interior of the needle 50, so that heat will be transmitted from the loop portion 60 to the composition as it flows through the needle into the body, thus achieving an extremely effective manner for maintaining a desired temperature of the composition while it is injected. Of course the wire used for the coil 56 and the loop 60 which extends into the needle is small enough in diameter to leave in the needle 50 a sufficient free space for substantially unrestricted flow of the composition into the body. If desired, an electrical insulation in the form of a coating or varnish or the like may be situated at the exterior of the wire coil in order to electrically insulate the latter.

Figure 4:
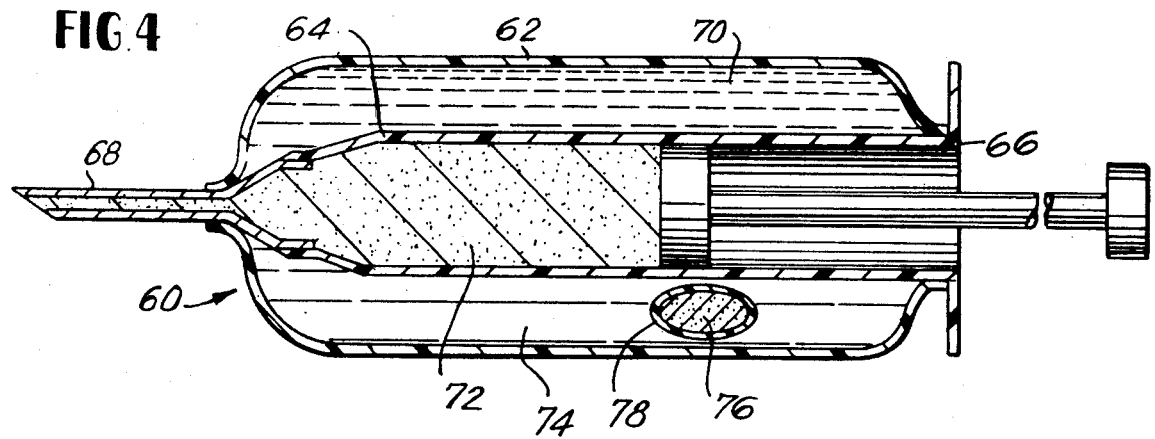
FIG. 4 is a sectional elevation schematically illustrating a still further embodiment of the invention.

The embodiment of the invention which is illustrated in FIG. 4 is exceedingly convenient inasmuch as it requires no outside source of power. According to this embodiment, there is situated at the exterior of the syringe means 60 a fluid-tight jacket 62 made of a material which is flexible, such as a suitable rubberized fabric, rubber sheet material, or any insulating plastic material which is fluid-tight and flexible. This outer jacket 62 is fluid-tightly fixed to the barrel 64 adjacent the outer end 66 thereof as well as to a part of the needle 68 which is joined with the barrel so as to define in this way a hollow interior space 70. Of course the injectable composition 72 is initially situated within the syringe means 60 in the manner described above.

Within the hollow space 70 are situated a reagent 74 as well as a second reagent 76. The second reagent 76 is separated from reagent 74 by a frangible barrier as by being situated in an initially closed capsule 78 made, for example, of a suitable frangible plastic material. For example, the reagent 74 may be water while situated within the capsule 78 is a reagent 76 which may be sodium hydroxide, for example. Thus with this construction all the operator need do is deform the flexible jacket 62 so as to break the capsule 78 and thus release the reagent 76 which upon contacting the reagent 74 will react therewith to generate heat which will then place the composition 72 in molten condition to enable the latter to be injected. Of course the selection of the reagent 74 and 76 is such that the desired temperature for the composition 72 will be provided upon breaking of the capsule 78.

Figure 5:
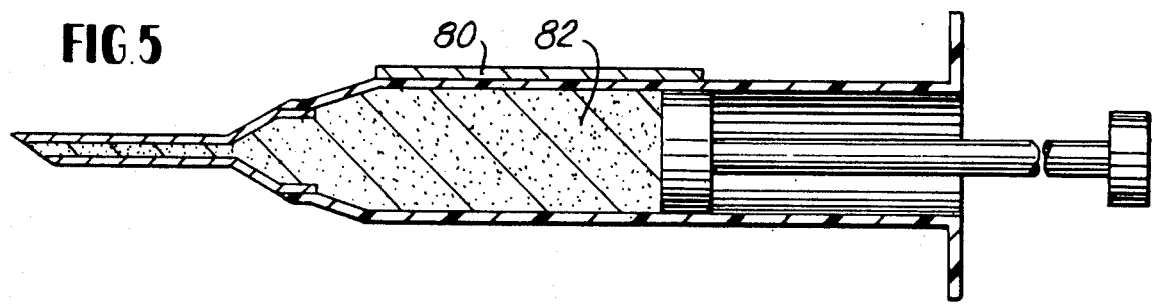
FIGS. 5–7 respectively illustrate different embodiments of indicating structures for indicating the temperature of the composition which is injected.
Figure 6:
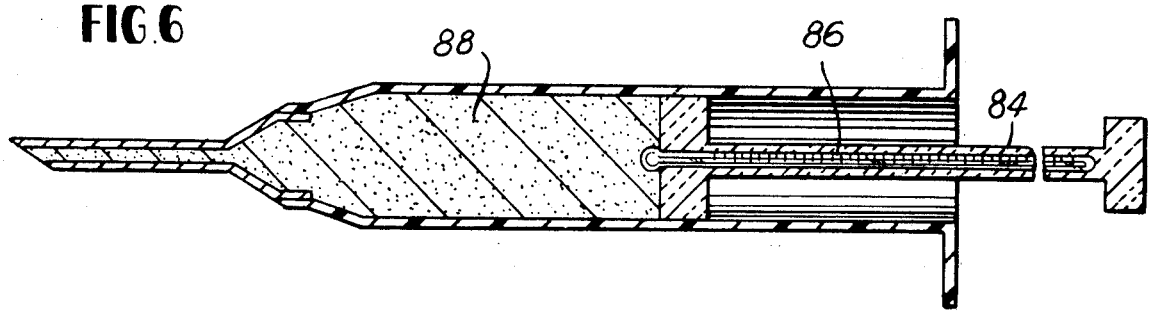
Figure 7:
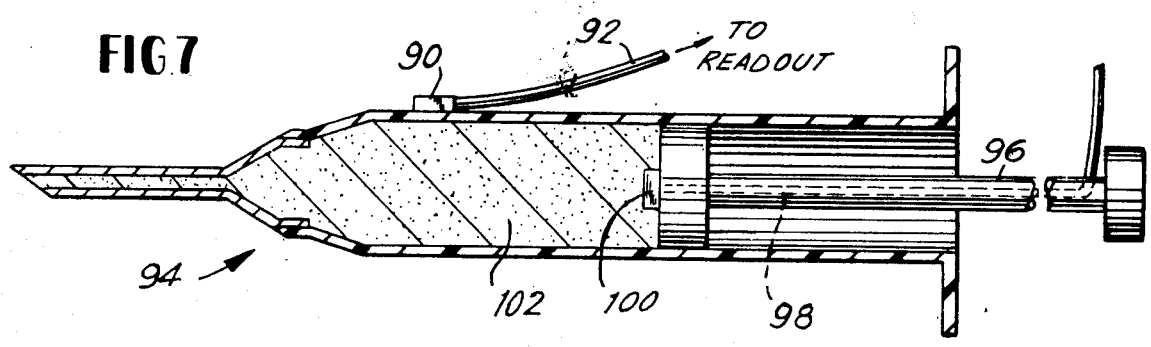

FIGS. 5-7 respectively illustrate different constructions suitable for indicating to the operator the temperature at which the composition is maintained in its molten condition.

Thus, the embodiment of FIG. 5 may be used, for example, with any of the above embodiments such as those of FIGS. 1 and 3, where the exterior surface of the syringe means is available. At the exterior surface of the syringe means there is situated a heat-sensitive sheet material 80 which has the property of changing its color when the composition 82 reaches the temperature at which it assumes its molten condition. Thus the operator will observe a color change of the sheet material 80 and will know that it is then time to proceed with injection of the composition 82.

With the embodiment of FIG. 6, the plunger 84 carries in its interior a thermometer 86. For this purpose the plunger is formed with an axial bore which receives the thermometer 86 with a suitable tight fit, and of course the plunger 84 itself is transparent being made of a material such as lucite, for example. The left end of the bore which receives the thermometer 86 is open, as viewed in FIG. 6, and the temperature-sensitive end of the thermometer 86 is exposed at this inner end of the plunger to directly engage the composition 88. Thus, with any of the above-described embodiments of the invention it is possible to provide a plunger 84 as shown in FIG. 6 with a thermometer which is visible through the plunger for indicating to the operator the temperature of the composition 88.

It is also possible to use for similar purposes an arrangement as shown in FIG. 7. According to this construction there is an exterior temperature-sensitive element 90 of known construction which is connected by a suitable conductor 92 to a readout device so that in this way it is possible to indicate to the operator the temperature at the exterior of the barrel of the illustrated syringe means 94. Also this embodiment may have an axially bored plunger 96 carrying in its interior a conductor 98 which extends to the exterior of the plunger to a suitable readout, and at the inner end of the plunger the conductor 98 is connected with an internal temperature-sensitive element 100 which directly engages the composition 102. Thus, with this embodiment of FIG. 7, which is used with any of the above-described embodiments, it is possible to utilize either one or both of the temperature-sensitive elements 90 and 100 in order to determine the temperature of the composition either by the temperature at the exterior of the barrel, when using element 90 alone or by the temperature of the composition itself, when using element 100 alone, although both of these elements can be used for indicating the difference in temperature between the interior and exterior.

A further feature of the invention which is capable of being used with any of the above-described embodiments is shown in FIG. 8. Thus FIG. 8 shows part of a barrel 104 of a syringe means, this barrel being provided with the threaded portion 106 to receive the needle. In the interior of the barrel adjacent the location where the needle will be received there is a metal insert 108 of high thermal conductivity, made of copper, for example. This insert 108 has the construction shown in FIG. 8 and is joined to the inner surface of the barrel 104 at the region where it is connected to the needle by a suitable sealing layer 110. In this case the material 108 will effectively conduct heat from the composition in the barrel so that heat will be provided at the insert 108 in a concentrated manner at the junction where the composition flows from the barrel into the needle so as to provide an exceedingly effective structure for introducing the composition in molten form into the body tissue. With the embodiment of FIG. 8 the barrel 104 can be made of a thermally insulating material.

FIG. 9 shows an embodiment similar to that of FIG. 8 in that in FIG. 9 the interior of the barrel 112 has joined thereto by a suitable sealant, for example, a metal insert 114 of high thermal conductivity such as an insert made, for example, of copper. In accordance with a further feature of the invention this insert is provided with a number of vanes 116 to increase the area of contact and the thermal transmission. The material of the insert 114 extends along the interior of the needle 118 which may be made of an insulating glass or plastic or which may be in the form of a suitable plating, the metal insert 114 itself forming the interior of the needle as illustrated. Thus with this embodiment the transmission of heat is very effective all the way through the interior of the needle 118 itself.

Referring now to FIG. 10, there is illustrated therein an embodiment of the invention which is similar to FIG. 9 in that the embodiment of FIG. 10 also includes in the barrel which is made of a suitable thermally insulating material an insert 122 of high thermal conductivity, such as an insert 122 made of copper and also having interior vanes 124 to increase the surface area and heat transmission. However, in this embodiment suitable small unillustrated spacers are situated between the insert and the barrel 120, on the one hand, as well as the needle 126 on the other hand. In this way there is created between the insert and the syringe means formed by the barrel 120 and needle 126 an interior air space 128 which provides an excellent thermal insulation. The outer wall of the needle 126 as well as the barrel 120 can be made of a suitable insulating material. Of course the injectable composition 130 is situated in the syringe means and upon elevation of the temperature of the insert 122, as by being heated from the molten medium 130, for example, it is possible to provide within the needle the temperature at which the compositions assumes a molten condition for easy injection into the body tissue. The composition in the barrels of the embodiments of FIGS. 8–10 can be heated to molten condition in any of the ways described above in connection with FIGS. 1–4, for example.

What is claimed is:

1. Apparatus for injecting into tissue of a living being at least one composition for affecting the health or appearance of the living being, with the composition being solid at the temperature of the body of the living being while being injectable in a molten condition when elevated to a temperature above the body temperature of the living being, comprising a syringe means having a hollow interior containing at least one of said compositions in solid form, and heating means operatively connected with said syringe means for elevating the temperature of the composition therein sufficiently to place said composition in molten injectable condition in preparation for injecting the composition into the tissue of the living being, said syringe means including a barrel member and a needle member connected therewith and extending from said barrel member, and said heating means being operatively connected at least with said needle member for maintaining said composition in a molten condition as it flows through said needle member while the latter is situated at least in part in tissue of the living being.

2. The combination of claim 1 and wherein said heating means is operatively connected with said needle member at the exterior thereof for transmitting heat through said needle member to place said composition in molten injectable form.

3. The combination of claim 2 and wherein said heating means is in the form of a heating coil engaging at least said needle member at the exterior thereof and being coiled around the latter.

4. The combination of claim 3 and wherein a thermostat means is operatively connected with said coil for regulating the temperature thereof.

5. The combination of claim 4 and wherein said syringe means includes a plunger for displacing the composition when it is in liquid, molten form out of the barrel member and needle member, and said coil being an electrical coil, said plunger having connected thereto an electrical means for completing a circuit through said coil in response to a given operation of said plunger.

6. Apparatus for injecting into tissue of a living being at least one composition for affecting the health or appearance of the living being, with the composition being solid at the temperature of the body of the living being while being injectable in a molten condition when elevated to a temperature above the body temperature of the living being, comprising a syringe means having a hollow interior containing at least one of said compositions in solid form, and heating means operatively connected with said syringe means for elevating the temperature of the composition therein sufficiently to place said composition in molten injectable condition in preparation for injecting the composition into the tissue of the living being, said syringe means including a barrel member and a needle member connected with and extending from said barrel member, and said heating means being operatively connected with at least one of said members, said heating means being operatively connected with said one member at the exterior thereof for transmitting heat through said one member to place said composition in molten injectable form, and heating means including a jacket connected to said one member and defining therewith a hollow interior space, said heating means including in said space a heating medium which changes phase while remaining at a constant temperature.

7. The combination of claim 1 and wherein said heating means is situated at the interior of said needle member directly in engagement with the composition.

8. The combination of claim 7 and wherein said heating means is in the form of an electrical heating coil situated in the interior of said needle and barrel members.

9. The combination of claim 8 and wherein an extension of said coil extends along the interior of the needle member.

10. Apparatus for injecting into tissue of a living being at least one composition for affecting the health or appearance of the living being, with the composition being solid at the temperature of the body of the living being while being injectable in a molten condition when elevated to a temperature above the body temperature of the living being, comprising a syringe means having a hollow interior containing at least one of said compositions in solid form, and heating means operatively connected with said syringe means for elevating the temperature of the composition therein sufficiently to place said composition in molten injectable condition in preparation for injecting the composition into the tissue of the living being, said syringe means including a barrel member and a needle member connected with and extending from said barrel member, and said heating means being operatively connected with at least one of said members, said heating means being operatively connected with said one member at the exterior thereof for transmitting heat through said one member to place said composition in molten injectable form, said heating means including an outer jacket operatively connected with said one member for defining therewith a hollow interior space, and said heating means including in said space reagents which react with each other to generate heat, at least one of said reagents being separated from the other by a barrier capable of being broken, and said jacket being flexible to enable the barrier to be broken by deformation of said jacket.

11. Apparatus for injecting into tissue of a living being at least one composition for affecting the health or appearance of the living being, with the composition being solid at the temperature of the body of the living being while being injectable in a molten condition when elevated to a temperature above the body temperature of the living being, comprising a syringe means having a hollow interior containing at least one of said compositions in solid form, so that upon transmission of heat to said composition the latter can have its temperature elevated to an extent sufficient to place the composition in molten injectable condition in preparation for injecting the composition into the tissue of the living being, and indicating means carried by said syringe means for indicating the temperature of said composition.

12. The combination of claim 11 and wherein said indicating means is in the form of a heat-sensitive material which changes color and which is carried by said syringe means so as to be visible.

13. The combination of claim 11 and wherein said indicating means is in the form of a thermometer.

14. The combination of claim 13 and wherein said syringe means includes a transparent plunger carrying said thermometer in the interior thereof so that said thermometer is visible through said plunger and said thermometer having a temperature-sensitive end engaging the composition.

15. The combination of claim 11 and wherein said indicating means is in the form of an external temperature-sensitive element carried by said syringe means and operatively connected to a readout.

16. The combination of claim 11 and wherein said indicating means is in the form of a temperature-sensitive element situated in the interior of said syringe means and extending from the interior to the exterior thereof for providing a readout of the temperature of the composition.

17. Apparatus for injecting into tissue of a living being at least one composition for affecting the health or appearance of the living being, with the composition being solid at the temperature of the body of the living being while being injectable in a molten condition when elevated to a temperature above the body temperature of the living being, comprising a syringe means having a hollow interior containing at least one of said compositions in solid form, and heating means operatively connected with said syringe means for elevating the temperature of the composition therein sufficiently to place said composition in molten injectable condition in preparation for injecting the composition into the tissue of the living being, said syringe means including a barrel of thermally insulating material, said barrel carrying in its interior adjacent a needle of said syringe means a material of high thermal conductivity capable of heated by a molten composition in the barrel.

18. The combination of claim 17 and wherein both the barrel and needle are of a thermal insulating material.

19. The combination of claim 17 and wherein said material of high thermal conductivity is copper.

20. The combination of claim 17 and wherein said material of high thermal conductivity is formed with vanes.

21. The combination of claim 18 and wherein said needle and barrel include a pair of walls separated from each other by an insulating air space.

22. The combination of claim 1 and wherein said syringe means contains a plurality of said compositions.

23. The combination of claim 10 and wherein said barrier is in the form of frangible capsule containing said one reagent.

24. The combination of claim 1 and wherein an indicating means is carried by said syringe means for indicating the temperature of said composition.

* * * * *